United States Patent
Yanaka et al.

(10) Patent No.: US 8,873,031 B2
(45) Date of Patent: Oct. 28, 2014

(54) METHOD AND APPARATUS FOR INSPECTING SURFACE OF A DISK

(71) Applicant: Hitachi High-Technologies Corporation, Tokyo (JP)

(72) Inventors: Yu Yanaka, Kamisato-machi (JP); Kiyotaka Horie, Kamisato-machi (JP); Fariz bin Abdulrashid, Kamisato-machi (JP)

(73) Assignee: Hitachi High-Technologies Corporation, Tokyo (JP)

( * ) Notice: Subject to any disclaimer, the term of this patent is extended or adjusted under 35 U.S.C. 154(b) by 119 days.

(21) Appl. No.: 13/758,243

(22) Filed: Feb. 4, 2013

(65) Prior Publication Data
US 2013/0258326 A1 Oct. 3, 2013

(30) Foreign Application Priority Data
Mar. 30, 2012 (JP) ................ 2012-079806

(51) Int. Cl.
*G01N 21/88* (2006.01)
*G06F 19/00* (2011.01)
*G01N 21/95* (2006.01)

(52) U.S. Cl.
CPC ..................... *G01N 21/95* (2013.01)
USPC ........... 356/237.2; 369/53.17; 702/40

(58) Field of Classification Search
USPC ............ 356/237.1–237.5; 702/35, 40; 369/53.17, 53.22
See application file for complete search history.

(56) References Cited

U.S. PATENT DOCUMENTS

| | | | |
|---|---|---|---|
| 6,876,445 B2 | 4/2005 | Shibuya et al. | |
| 7,898,652 B2* | 3/2011 | Hariyama et al. | 356/237.2 |
| 8,781,758 B2* | 7/2014 | Serikawa et al. | 702/40 |
| 2011/0141598 A1 | 6/2011 | Mochizuki | |
| 2012/0081701 A1* | 4/2012 | Sasazawa et al. | 356/237.2 |
| 2013/0258320 A1* | 10/2013 | Funaki et al. | 356/73 |
| 2014/0043603 A1* | 2/2014 | Yanaka et al. | 356/237.5 |

FOREIGN PATENT DOCUMENTS

| | | | |
|---|---|---|---|
| JP | 2000-180376 A | 6/2000 | |
| JP | 2001-066263 A | 3/2001 | |
| JP | 2006-352173 A | 12/2006 | |
| JP | 2011-122998 A | 6/2011 | |

* cited by examiner

*Primary Examiner* — Hoa Pham
(74) *Attorney, Agent, or Firm* — Mattingly & Malur, PC

(57) ABSTRACT

A disk surface inspection method for detecting a circle scratch defect, separately from sporadically existing scratch defects. In the method, the sample is irradiated with light, regular reflection light reflected from the sample is detected, scattered light in the vicinity of the regular reflection light is detected separately from the regular reflection light, scattered light, scattered in a high angle direction greater than the direction of the regular reflection light is detected, and the defects on the surface of the sample are detected by processing a regular reflection light detection signal, a low-angle scattered light detection signal and a high-angle scattered light detection signal to extract defect candidates, and regarding the extracted defect candidates, a circumferential defect is extracted based on the ratio of defect candidates in a circumferential direction within a predetermined width in a radial direction from the center of the sample.

10 Claims, 4 Drawing Sheets

METHOD AND APPARATUS FOR INSPECTING SURFACE OF A DISK

BACKGROUND

The present invention relates to a disk surface inspection method and its apparatus for optically inspecting defects on a sample surface.

As a magnetic disk substrate, an aluminum (Al) substrate or a glass substrate is used. As the glass substrate, crystallized glass (SX) or amorphous glass (MEL) is used in accordance with purpose, and as the respective types of glass, plural types of glass having different ingredients are used.

In the glass substrate, a concentric circular continuous flaw or a discontinuous flaw occurs in some cases in the middle of process steps. Unless the step that caused the concentric circular flaw on the glass substrate is specified and a countermeasure is conducted quickly, a large number of glass substrates having the concentric circular flaw flow the production line. There is a probability of mass production of defective products.

On the other hand, the defects on the surface of the glass substrate are optically inspected using an optical inspection device. In the device for inspecting the surface of the glass substrate, there is a need for classification of detected defects for the purpose of distribution to high level process management and process step improvement. A detection optical system of a device for inspecting the surface of a magnetic disk substrate is generally provided with plural detectors. In addition to classification of minute defects using detection signals from these plural detectors, classification of defects is performed based on the feature of defect distribution shape in the magnetic disk surface.

As a conventional device for inspecting defects on the surface of a magnetic disk, Japanese Patent Application Laid-Open Publication No. 2000-180376 discloses irradiating a magnetic disk as an inspection subject sample with laser, receiving reflection light and scattered light from the magnetic disk surface with plural detectors, and classifying minute defects under photoreception conditions of the respective photoreceptors. Further, flat surface continuity of detected minute defects is determined, and classification is performed by defect length, linear defect and solid defect.

Further, Japanese Patent Application Laid-Open Publication No. 2001-66263 discloses a disk surface inspection device which detects a circle scratch formed on a disk surface as a defect using a light condensing unit with small solid angle provided in an elevation angle position corresponding to the directivity of predetermined scattered light on the same optical axis as that of laser emitted on the disk surface.

Further, Japanese Patent Application Laid-Open Publication No. 2006-352173 discloses defect classification in accordance with defect distribution status, including detecting linearly arrayed defects by Hough transform using defect position information obtained by inspection of the surface of a semiconductor wafer.

Further, Japanese Patent Application Laid-Open Publication No. 2011-122998 discloses generating a histogram of number of defects by substrate radius, and detecting circular scratch and island defect separately from other defects.

SUMMARY

The conventional optical inspection device for optically inspecting defects on the surface of a disk substrate irradiates the substrate with light, detects reflection light and scattered light from the substrate with plural detectors arranged in different elevating angle directions, and compares detection signal levels with a predetermined threshold value. When a signal greater than the threshold value is detected, it is determined that a defect has been detected.

Among defects, a circle scratch defect which occurs in a concentric circular shape on a disk becomes a serious defective factor in the disk. Regarding this circle scratch defect which occurs in a concentric circular shape, since it is difficult to detect the entire defect, the conventional optical inspection device detects this defect as sporadic short-length scratches in a concentric circular shape.

In the disk surface inspection devices disclosed in Japanese Patent Application Laid-Open Publication No. 2000-180376 and Japanese Patent Application Laid-Open Publication No. 2001-66263, it is possible to detect a continuously occurred circular flaw. However, since there is no consideration of detection of discretely occurred circle scratch information as one defect, it is impossible to discriminate the above-described discretely-occurred circle scratch from an independently-occurred general scratch.

Further, in the defect data analysis method disclosed in Japanese Patent Application Laid-Open Publication No. 2006-352173, defects distributed in a ring shape are detected. However, when short length scratch defects sporadically exist in a concentric circular shape, there is no description of discrimination as a circle scratch which occurs in a concentric circular shape, separately from the defects distributed in the ring shape.

Further, Japanese Patent Application Laid-Open Publication No. 2011-122998 discloses generation of a histogram of the number of defects by substrate radius and detection of circular flaws and island defects separately from other defects. However, there is no description of extracting a circle scratch defect which occurs in a concentric circular shape from the circular flaws.

The present invention addresses the problems of the above-described conventional techniques, and provides a disk surface inspection method and its apparatus which enables detection of a circle scratch defect which occurs in a concentric circular shape on a disk, separately from scratch defects which sporadically exist on the disk surface.

To address the above-described problem, the present invention provides a disk surface inspection apparatus, including: a stage unit that is capable of rotating while holding a magnetic medium disk as a sample and capable of moving in a direction vertical to a rotation central axis; an illumination unit that irradiates a front surface of the sample placed on the stage unit with light; a regular reflection light detection unit that detects regular reflection light reflected from the front surface of the sample irradiated with light by the illumination unit; a low-angle scattered light detection unit that detects scattered light in the vicinity of the regular reflection light reflected from the front surface of the sample irradiated with light by the illumination unit, and separated from the regular reflection light; a high-angle scattered light detection unit that detects scattered light scattered, from the sample irradiated with light by the illumination unit, in a high angle direction greater than the direction of the regular reflection light with respect to a normal line direction of the sample; and a processing unit that processes an output signal from the regular reflection light detection unit, an output signal from the low-angle scattered light detection unit and an output signal from the high-angle scattered light detection unit, and detects defects on the surface of the sample, wherein the processing unit further includes: a defect candidate extraction unit that processes the output signal from the regular reflection light detection unit, the output signal from the low-angle scattered light detection unit, and the output signal from the high-angle scattered light detection unit, and extracts defect candidates; and a circumferential defect extraction unit that extracts, regarding the defect candidates extracted by the defect candidate extraction unit, a circumferential defect based on a ratio of a circumferential direction where the defect candidates exist within a predetermined width in a radial direction from a center of the sample.

Further, to address the above-described problem, the present invention provides a disc surface inspection method, including the steps of: moving a magnetic medium disk as a sample in a direction vertical to a rotation central axis while rotating it; irradiating a front surface of the sample with light; detecting regular reflection light reflected from the sample irradiated with light; detecting scattered light in the vicinity of the regular reflection light reflected from the sample irradiated with light, separately from the regular reflection light; detecting scattered light scattered, from the sample irradiated with light, in a high angle direction greater than the direction of the regular reflection light with respect to a normal line direction of the sample; and processing a signal obtained by detecting the regular reflection light, a signal obtained by detecting the low-angle scattered light and a signal obtained by detecting the high-angle scattered light, and detecting defects on the surface of the sample, wherein, defects on the surface of the sample are detected by: processing the signal obtained by detecting the regular reflection light, the signal obtained by detecting the low-angle scattered light, and the signal obtained by detecting the high-angle scattered light, and extracting defect candidates; and regarding the extracted defect candidates, extracting a circumferential defect based on a ratio of a circumferential direction where defect candidates exist within a predetermined width in a radial direction from a center of the sample.

According to the disk surface inspection apparatus of the present invention, it is possible to discriminate a circle scratch which discontinuously occurs in a concentric circular shape on a disk from general scratches which independently and sporadically occur. With this arrangement, it is possible to infallibly detect a conventionally-missed circle scratch, to specify a process step to cause the occurrence of the circle scratch and quickly take a countermeasure.

These features and advantages of the invention will be apparent from the following more particular description of preferred embodiment of the invention, as illustrated in the accompanying drawings.

DESCRIPTION OF THE PREFERRED EMBODIMENTS

The present invention is an apparatus for inspecting defects on the surface of a glass substrate. Upon irradiation of the substrate with illumination light, regular reflection light or scattered light from the substrate is detected, and defect candidates are extracted. From the extracted defect candidates, first, a defect in a concentric circle shape is extracted. Next, regarding the other defect candidates than the concentric circular defect, defect types are classified in correspondence with feature of the respective defect candidates.

Hereinbelow, an embodiment of the present invention will be described using the drawings.

Figure 1:
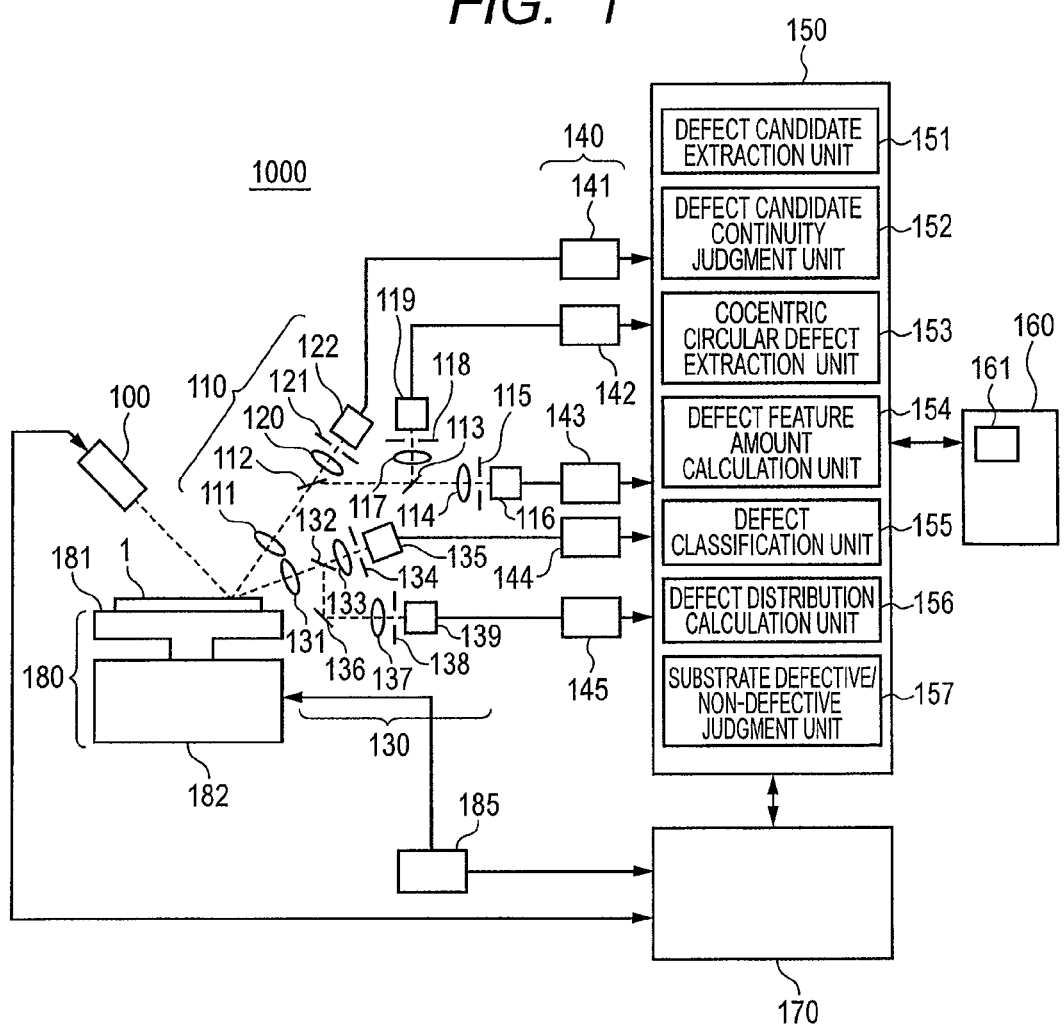
FIG. 1 is a block diagram showing the configuration of the entire concept of a disk surface defect inspection apparatus according to an embodiment of the present invention.

FIG. 1A shows a configuration of a disk surface defect inspection apparatus 1000 according to the present embodiment. A sample 1 as an inspection subject is a magnetic disk substrate formed of a glass material. The disk surface defect inspection apparatus 1000 has an illumination unit 100 to irradiate the sample 1 with illumination light, a low-angle detection optical system 110 to collect and detect light reflected or scattered from the sample 1 irradiated with light in a low angle direction (direction where an angle formed with a normal line direction of the surface of the sample 1 is small), a high-angle detection optical system 130 to collect and detect light reflected or scattered from the sample 1 in a high angle direction (direction where an angle formed with the normal line direction of the surface of the sample 1 is large), an A/D conversion unit 140 to amplify respective analog detection signals, as the reflected or scattered light from the sample 1 detected with and outputted from detectors 116, 119 and 122 of the low-angle detection optical system 110 and detectors 135 and 139 of the high-angle detection optical system 130, and convert the signals into digital signals (A/D conversion), a processing unit 150 to receive the signals from the respective detectors converted with the A/D converter 140 and processes the signals, an input/output unit 160 to input processing condition of the processing unit 150 and output the result of processing, an entire control unit 170 to control the entire disk surface defect candidate inspection apparatus 1000, and a stage unit 180, controlled with a stage control unit 185, to move the sample 1 in one direction while holding the sample 1 and rotating it.

The illumination unit 100 has a laser light source to output laser having a desired wavelength.

The low-angle detection optical system 110 is an optical system to detect reflected or scattered light, irradiated by the illumination unit 100 and reflected or scattered from the surface of the sample 1, including regular reflection light advanced in the low angle direction within a direction indicated with a dotted line. The low-angle detection optical system 110 has an objective lens 111 to collect the reflected or scattered light, including regular reflection light advanced in the low angle direction from the surface of the sample 1; a mirror 112 to reflect the regular reflation light from the sample 1 in the light collected with the objective lens 111; a beam splitter 113 to split the optical path of the regular reflection light from the sample 1 reflected by the mirror 112 into two paths; a convergence lens 114 to converge the regular reflection light passed through the beam splitter 113; a pin hole plate 115, having a pin hole positioned in a convergence point of the regular reflection light with the convergence lens 114 to pass the converged regular reflection light, to block stray light other than the regular reflection light; a first regular reflection light detector 116 to detect the regular reflection light passed through the pin hole of the pin hole plate 115; a convergence lens 117 to converge the regular reflection light reflected by the beam splitter 113; a pin hole plate 118, having a pin hole positioned in a convergence point of the regular reflection light with the convergence lens 117 to pass the converged regular reflection light, to block stray light other than the regular reflection light; a second regular reflection light detector 119 to detect the regular reflection light passed through the pin hole of the pin hole plate 118; a convergence lens 120 to converge the light which is not reflected by the mirror 112 (the scattered light from the sample 1) in the light collected by the objective lens 111; a pin hole plate 121, having a pin hole positioned in a convergence point of the regular reflection light by the convergence lens 120 to pass the converged regular reflection light, to block unconverged light; and a low-angle detector 122 to detect the light passed through the pin hole of the pin hole plate 121.

The beam splitter 113 passes the majority (e.g. 90%) of the incident regular reflection light so as to detect it with the detector 116, and reflects a part (e.g. 10%) of the incident regular reflection light so as to detect it with the detector 119. In this arrangement, when the regular reflection light from the sample 1 is weak, the signal detected by the detector 116 is processed. On the other hand, when the regular reflection light from the sample 1 is strong, as the detector 116 is saturated, the signal detected by the detector 119 is processed. By the detection of the regular reflection light in this manner, it is possible to detect the regular reflection light in wider dynamic range in comparison with detection with one detector.

The high-angle detection optical system 130 has an objective lens 131 to collect reflected or scattered light advanced in the high angle direction from the surface of the sample 1 caused by the light emitted from the illumination unit 100; a beam splitter 132 to split the optical path of the light collected by the objective lens 131; a convergence lens 133 to converge the light passed through the beam splitter 132; a pin hole plate 134, having a pin hole positioned in a convergence point of the convergence lens 133 to pass the converged regular reflection light, to block unconverged light; a first high-angle detector 135 to detect the light passed through the pin hole of the pine hole plate 134; a mirror 136 to change the optical path of the light reflected from the beam splitter 132; a convergence lens 137 to converge the reflection light, the optical path of which has been changed by the mirror 136, from the beam splitter 132; a pin hole plate 138, having a pin hole positioned in a convergence point of the convergence lens 137 to pass the converged light, to block unconverged light; and a second high-angle detector 139 to detect the light passed through the pin hole plate 138.

The beam splitter 132 passes the majority (e.g. 90%) of the incident scattered light so as to detect it with the detector 135 and reflects a part (e.g. 10%) of the incident scattered light so as to detect it with the detector 139. In this arrangement, when the scattered light from the sample 1 is weak, the signal detected by the detector 135 is processed. On the other hand, when the scattered light from the sample 1 is strong, as the detector 135 is saturated, the signal detected by the detector 139 is processed. By the detection of the regular reflection light in this manner, it is possible to detect the reflection light in wider dynamic range in comparison with detection with one detector.

The analog signals outputted from the respective detectors 116, 119, 122, 135 and 139 by the detection of the light reflected or scattered from the surface of the sample 1, are amplified and A/D converted with A/D converters 141 to 145 of the A/D conversion unit 140, and inputted into the processing unit 150.

The processing unit 150 has a defect candidate extraction unit 151 to receive the signals, outputted from the respective detectors 116, 119, 122, 135 and 139 and A/D converted by the A/D converter 140, and detect defect candidates; a defect candidate continuity judgment unit 152 to, regarding the defect candidates detected by the defect candidate extraction unit 151, judge connection/continuity of the respective defect candidates using position information on the sample 1 where the respective defect candidates have been detected, obtained from a stage control unit 185 and a stage 180; a concentric-circular defect extraction unit 153 to extract defects arrayed in a concentric circular shape (circle scratch) among the defect candidates judged to have connection/continuity by the defect candidate connection/continuity judgment unit 152; a defect feature amount extraction unit 154 to, among the respective defect candidates judged to have connection/continuity by the defect candidate connection/continuity judgment unit 152, except for the defects arrayed in a concentric-circular shape (circle scratch) extracted by the concentric-circular defect extraction unit 153, extracts feature amounts; a defect classification unit 155 to classify the defect candidates according to the feature amounts obtained from the defect feature amount extraction unit 154, by defect type based on feature amount; and a substrate rank judgment unit 156 to obtain the distribution and the number of defects on the sample 1 by defect type, classified by the defect classification unit 155, and judge the rank of the sample 1.

The processing unit 150 is connected to the input/output unit 160, having a display screen 161, to input an inspection condition and output the result of inspection. Further, the processing unit 150 and the input/output unit 160 are connected to the entire control unit 170. The entire control unit 170 controls the stage control unit 185 to drive-control the stage unit 180 having a rotary stage 181 to hold and rotate the sample 1, and a translatory stage 182 movable in at least one direction within a plane of rotation of the sample 1, the illumination unit 100, the processing unit 150 and the input/output unit 160.

Figure 2:
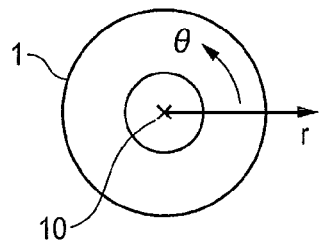
FIG. 2 is a plan view of a disk as a sample.

In the above-described configuration, by controlling the stage control unit 185 with the entire control unit 170 to drive the rotary stage 181 and the translatory stage 182 of the stage unit 180, the sample 1 placed on the stage unit 180 is rotated in a θ direction as shown in FIG. 2, and is moved in a direction orthogonal to a rotational center 10 (in the radius (r) direction of the sample 1) at a constant speed.

In this state, the illumination unit 100 irradiates the surface of the sample 1, placed and rotated on the stage unit 180, with laser. Then, among the light reflected or scattered from the surface of the sample 1 and advanced toward the objective lens 111, the regular reflection light is detected by the first regular refection light detector 116 and the second regular reflection light detector 119, and the scattered light in the periphery of the regular reflection light is detected by the low angle detector 122. Further, the scattered light from the surface of the sample 1 and advanced toward the objective lens 131 of the high-angle detection optical system 130 is detected by the first high-angle detector 135 and the second high-angle detector 139.

By performing this inspection in a spiral shape on the surface of the sample 1 from the outer periphery to the inner periphery of the sample 1, while translatory moving and rotating the sample 1, it is possible to inspect the whole surface of the sample 1 on the front side. Further, by reversing the sample 1 using a substrate reversing mechanism (not shown) so as to set the uninspected rear surface as a top surface and performing the inspection similar to that of the front side surface, it is possible to inspect the both surfaces of the sample.

Note that in the present example, the pin hole plates 115, 118, 121, 134 and 138 are used to block stray light in the low-angle detection optical system 110 and the high-angle detection optical system 130. However, when the sample 1 is illuminated with polarized-light by inserting a polarizing plate in the optical path of the laser emitted from the illumination light source 100, the pin hole plates 115, 118, 121, 134 and 138 may be replaced with polarizing filters. Further, when a single wavelength laser is used as laser emitted from the illumination light source 100, wavelength selection filters may be used in place of the pin hole plates 115 118, 121, 134 and 138. Further, it may be arranged by using both of the polarizing filters and the wavelength selection filters, light having a particular polarized component with a particular wavelength is passed through both of the filters.

Figure 3:
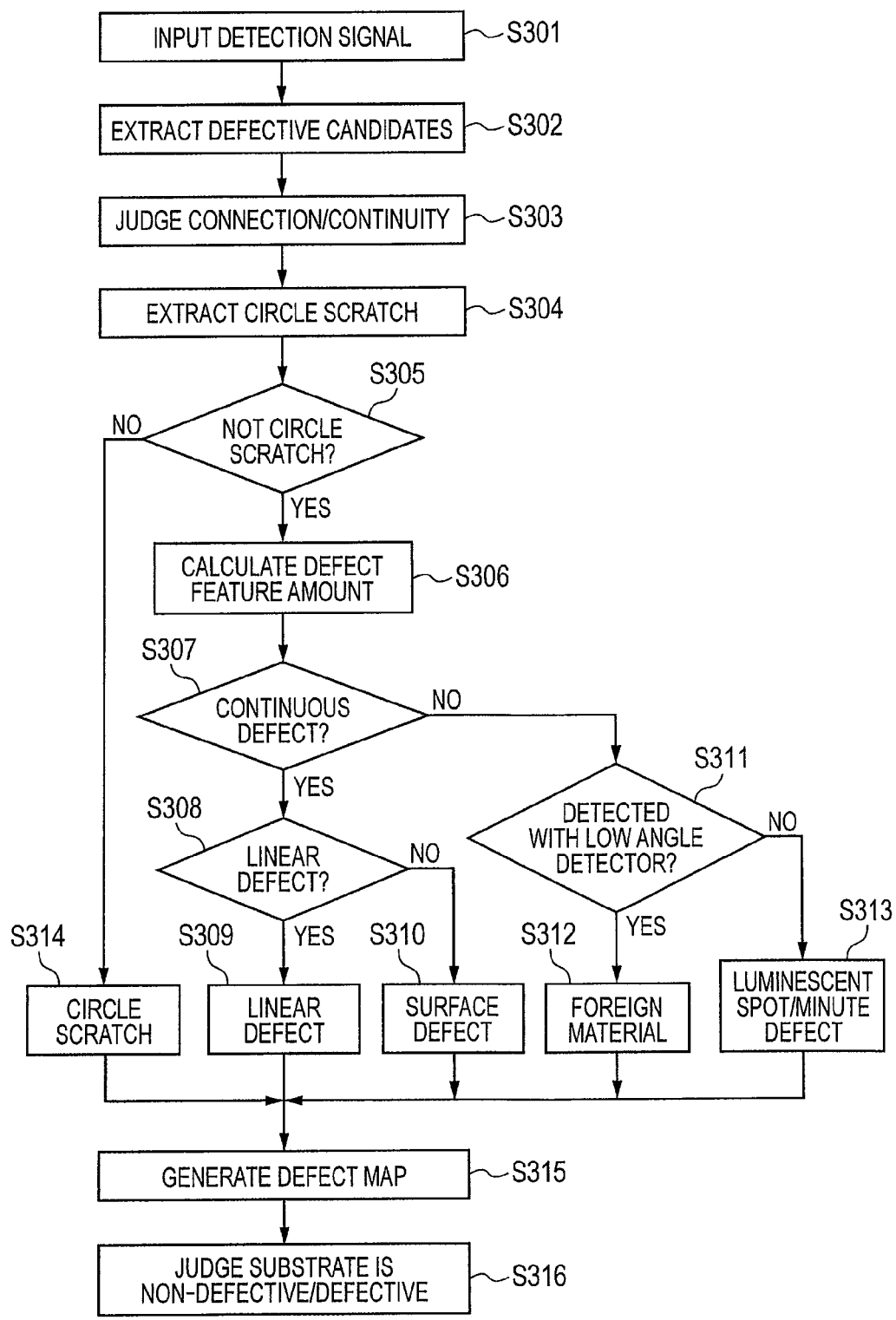
FIG. 3 is a flowchart showing a procedure of inspection in the embodiment of the present invention.

Next, a procedure of processing the signals outputted from the respective detectors 116, 119, 122, 135 and 139 and inputted into the processing unit 150 will be described using FIG. 3.

The detection signals outputted from the respective detectors 116, 119, 122, 135 and 139 and A/D converted with the A/D converters 141 to 145 are inputted into the processing unit 150 (S301).

First, the defect candidate extraction unit 151 compares the signal levels of the detection signals, inputted in the processing unit 150 from the A/D converters 141 to 145, with a previously-set threshold value. Then, signals having a level higher than the threshold value are extracted, as defect candidates, linked with position information on the sample 1 (rotational angle (θ) information and substrate radius (r) direction position information of the stage 180) of defect candidates obtained from an unshown detection system of the stage control unit 185 and the sage unit 180 (S302).

Next, regarding the defect candidates extracted by the defect candidate extraction unit 151, the defect candidate continuity judgment unit 152 judges the connection/continuity of the respective defect candidates using the position information on the sample 1 (S303). The defect candidates judged that they have connection/continuity are subjected to the following processing as one defect.

Next, at S303, regarding the defect candidates judged by the defect candidate continuity judgment unit 152 to have connection/continuity, the concentric circular defect extraction unit 153 extracts continuous or noncontiguous concentric-circular shaped defect (circle scratch) in the same radial position of the sample 1 (S304).

Figure 4A:
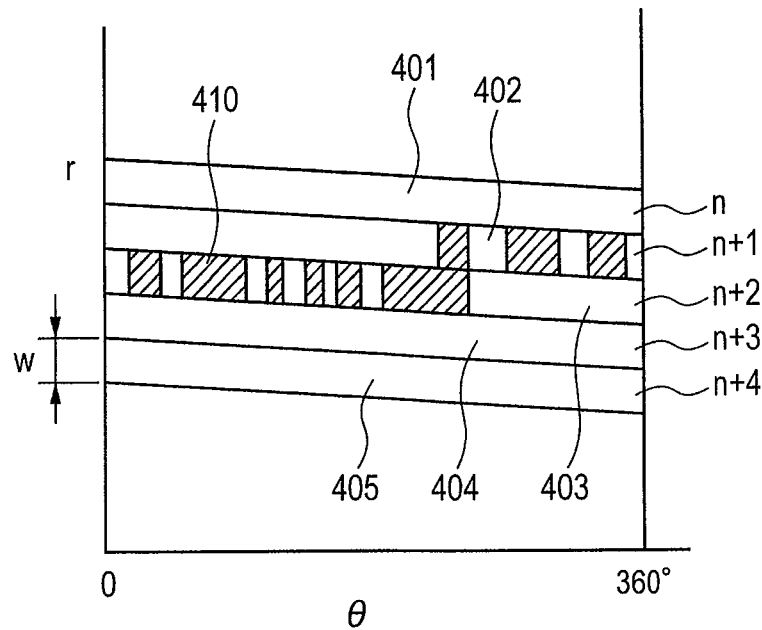
FIG. 4A is a graph in a case where a sample surface is inspected in a spiral shape and a circle scratch is detected, showing outputs from respective detectors, in correspondence with inspection regions in respective rotations of the sample, plotted in r-θ coordinate system.

FIG. 4A shows inspection regions and plotted detection signals of the respective detectors from the n-th rotation to the n+4th rotation of the sample 1. The lateral axis indicates the rotation angle (θ) of the sample 1, and the vertical axis, a position (r) of the sample 1 in the radial direction from the center. As the respective detectors inspect the surface of the sample 1 in spiral shape by a width w in the radial direction of the sample 1, when the inspection results are represented in an r-θ coordinate system, inspection regions 401 to 405 by each rotation are represented as inclined band regions with the width w as shown in FIG. 4A. Numeral 410 denotes a position where a defect has been detected.

Figure 4B:
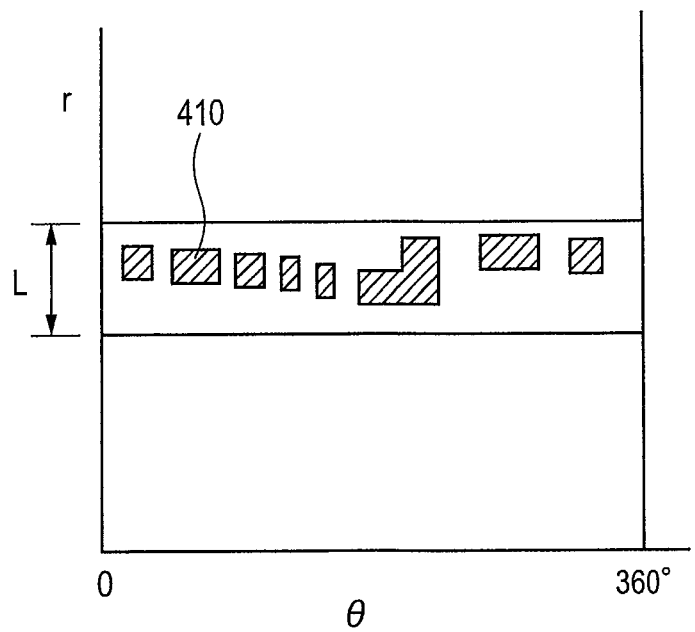
FIG. 4B is a graph where the results in FIG. 4A, without display of inspection regions in the respective rotations of the sample, plotted in the r-θ coordinate system.

When defects corresponding to the circle scratch detected in this manner are plotted in the r-θ coordinate system, the result is represented as shown in FIG. 4B. The circle scratch exists in a concentric circular region on the surface of the sample 1. As the inspection region is formed in a spiral shape, the defects corresponding to the circle scratch, which are also corresponding to the spiral inspection region, are detected in a way that the positions in the r direction are changed. Accordingly, to extract the defects corresponding to the circle scratch from the defects plotted in the r-θ coordinate system, a region having a double of the width w of the inspection region indicated with an interval L in FIG. 4B or greater than the double of the width w is detected while it is sequentially shifted in the r direction on the r-θ coordinate plane. Then, when the total of the lengths of the defects detected within the width L in the θ direction is greater than a previously-set ratio with respect to 1 cycle 360 degree (when the density in the θ direction is higher than a previously-set reference value) in a position in the r direction, it is determined that a concentric circular defect (circle scratch) exists in the position in the r direction.

On the other hand, when the total of the lengths of the defects detected within the width L in the θ direction is less than the previously-set ratio with respect to 1 cycle 360 degree (when the density in the θ direction is lower than the previously-set reference value) in a position in the r direction, it is determined that no concentric circular defects (circle scratch) exists in the position in the r direction.

Among the defect candidates judged by the defect candidate continuity judgment unit 152 at S303 that they have connection/continuity, except the defects extracted with the concentric circular defect extraction unit 153 at S304 as concentric circular defect (S305), i.e. regarding the defect candidates except the concentric circular defect, the defect feature amount calculation unit 154 calculates a defect feature amount including the defect size (the length in the r direction, the length in the θ direction and the width of the defect), the area and the like (S306). At this time, regarding the defect candidates judged with the defect candidate continuity judgment unit 153 that they have connection/continuity, the feature amount is calculated as one defect.

Finally, regarding the defects the feature amount of which has been calculated, the defect classification unit 155 checks whether or not they are a continuous defect (S307). When it is determined that they are a continuous defect, it is checked whether or not they are a linear defect (S308). When the continuous defects do not have spread within the plane, it is determined that they are a linear defect (S309). When it is determined that the continuous defects have spread within the plane, it is determined that they are a planar defect (S310).

On the other hand, when it is determined at S307 that they are not a continuous defect, it is checked whether or not the low angle detector 122 also has detected the defects (S311). When it is determined that the low angle detector 122 also has detected the defects, it is determined that they are foreign material defects (S312). When it is determined that the low angle detector 122 did not detect the defects, it is determined that they are luminescent spots (minute defects) (S313).

Further, the defects determined NO at S305 are judged as a circle scratch (S314).

Next, the distribution calculation unit 156 obtains the distribution on the sample 1 by defect type classified by the defect classification unit 155, and generates a defect map by the defect type (S315).

Finally, the defect classification unit 155 compares the defect types classified at S305 to S314 and the number of defects by the defect type with a previously-set reference value, to perform defective/non-defective judgment of the sample (substrate) 1 (S316).

The input/output unit 160 receives information from the processing unit 150 including the circle scratch information extracted with the concentric circular defect extraction unit 152 at S304 and the defect map information by defect type generated with the defect distribution calculation unit 156 at S315. Then as shown in FIG. 5, the input/output unit 160 displays the inspection result on the display screen 161.

Figure 5:
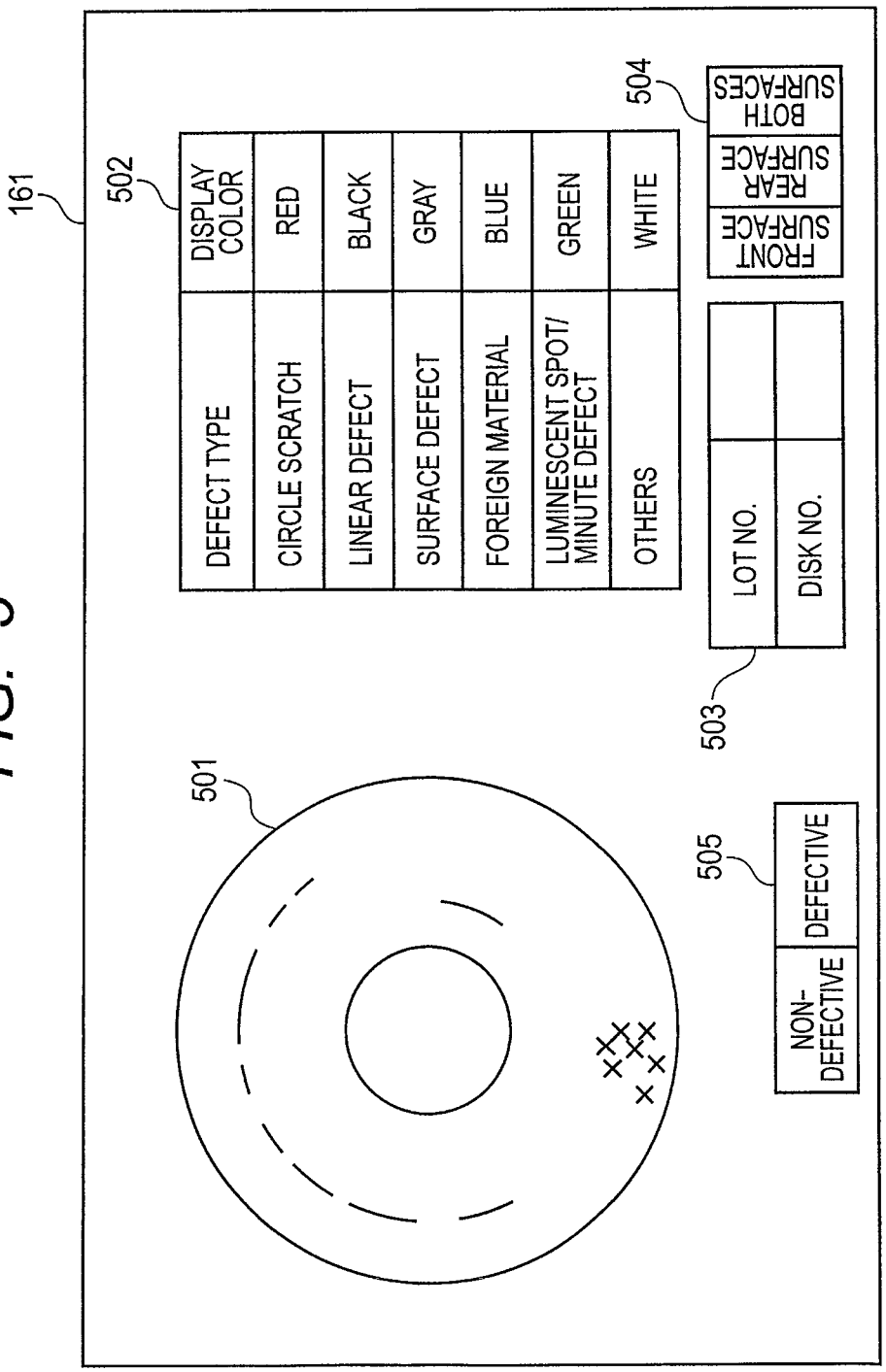
FIG. 5 is a front view of a display screen where the result of the inspection in the embodiment of the present invention is outputted.

FIG. 5 shows an example of the inspection result displayed on the display screen 161 of the input/output unit 160. The distribution of defects on the sample 1 is displayed on a map 501 and a list 502 of display color by defect type displayed on the map 501 is displayed adjacent the map 501. When a particular defect type is selected with a pointer or the like on the list 502, defects corresponding to the selected defect type are enhanced in comparison with other defects on the map 501. Further, on the display screen 161, a lot No. of the sample 1 currently displayed on the map 501 in the production line and a disk No. indicating the sample 1 itself are displayed in a display field 503.

Further, on the display screen 161, a display surface selection button 504 to select a surface of the sample displayed on the map 501 is displayed, and it is possible to select the front surface, the rear surface or the both surfaces, as the surface of the sample displayed on the map 501. Further, the result of defective/non-defective judgment of the sample (substrate) 1 judged by the defective/non-defective judgment unit 157 at S314 is displayed on a judgment result display unit 505.

According to the present embodiment, it is possible to detect a circle scratch formed with discontinuous defects, which has been conventionally overlooked, and further, without erroneous judgment as another type of defect.

As described above, the invention made by the present inventors has been particularly explained based on the embodiment. However, the present invention is not limited to the above-described embodiment, and various changes can be made within a range without departing from the subject matter. That is, an example where a part of the constituent elements (steps) described in the above embodiment is replaced with a step or unit having an equivalent function, or an example where a part of unsubstantial function is omitted, are included in the present invention.

The invention claimed is:

1. A disk surface inspection apparatus, comprising:
    a stage unit that is capable of rotating while holding a magnetic medium disk as a sample and capable of moving in a direction vertical to a rotation central axis;
    an illumination unit that irradiates a front surface of the sample placed on the stage unit with light;
    a regular reflection light detection unit that detects regular reflection light reflected from the front surface of the sample irradiated with light by the illumination unit;
    a low-angle scattered light detection unit that detects scattered light in the vicinity of the regular reflection light reflected from the front surface of the sample irradiated with light by the illumination unit, and separated from the regular reflection light;
    a high-angle scattered light detection unit that detects scattered light scattered, from the sample irradiated with light by the illumination unit, in a high angle direction greater than the direction of the regular reflection light with respect to a normal line direction of the sample; and
    a processing unit that processes an output signal from the regular reflection light detection unit, an output signal from the low-angle scattered light detection unit and an output signal from the high-angle scattered light detection unit, and detects defects on the surface of the sample,
    wherein the processing unit further includes:
        a defect candidate extraction unit that processes the output signal from the regular reflection light detection unit, the output signal from the low-angle scattered light detection unit, and the output signal from the high-angle scattered light detection unit, and extracts defect candidates; and
        a circumferential defect extraction unit that extracts, regarding the defect candidates extracted by the defect candidate extraction unit, a circumferential defect based on a ratio of a circumferential direction where the defect candidates exist within a predetermined width in a radial direction from a center of the sample.

2. The disk surface inspection apparatus according to claim 1, wherein the processing unit further includes a defect candidate continuity judgment unit that judges, regarding the defect candidates extracted with the defect candidate extraction unit, connection/continuity of the defect candidates based on position information of the defect candidates on the sample, and wherein the circumferential defect extraction unit extracts the circumferential defect using the connection/continuity information of the defect candidates judged by the defect candidate continuity judgment unit.

3. The disk surface inspection apparatus according to claim 2, wherein regarding a defect not judged by the defect candidate continuity judgment unit that the connection/continuity exists in a circumferential shape, the circumferential defect extraction unit extracts it as a circumferential defect when the ratio in the circumferential direction in which plural defect candidates exist in the range of the predetermined width in the radial direction from the center of the sample is equal to or greater than a previously set ratio.

4. The disk surface inspection apparatus according to claim 1, wherein the processing unit further includes:
    a feature amount calculation unit that calculates feature amounts of defect candidates other than that extracted as a circumferential defect by the circumferential defect extraction unit, from the defect candidates extracted by the defect candidate extraction unit; and a defect classification unit that classifies the defect candidates as a linear defect, a surface defect, and a plurality of types including foreign material, based on the feature amounts of the defect candidates calculated by the feature amount calculation unit.

5. The disk surface inspection apparatus according to claim 1, further comprising an input/output unit having a display screen, wherein the plurality of types of defects including the circumferential defect on the sample, processed by the processing unit, are displayed on a map, on the display screen.

6. A disc surface inspection method, comprising the steps of:
    moving a magnetic medium disk as a sample in a direction vertical to a rotation central axis while rotating it;
    irradiating a front surface of the sample with light;
    detecting regular reflection light reflected from the sample irradiated with light;
    detecting scattered light in the vicinity of the regular reflection light reflected from the sample irradiated with light, separately from the regular reflection light;
    detecting scattered light scattered, from the sample irradiated with light, in a high angle direction greater than the direction of the regular reflection light with respect to a normal line direction of the sample; and
    processing a signal obtained by detecting the regular reflection light, a signal obtained by detecting the low-angle scattered light and a signal obtained by detecting the high-angle scattered light, and detecting defects on the surface of the sample,
    wherein, defects on the surface of the sample are detected by:

processing the signal obtained by detecting the regular reflection light, the signal obtained by detecting the low-angle scattered light, and the signal obtained by detecting the high-angle scattered light, and extracting defect candidates; and regarding the extracted defect candidates, extracting a circumferential defect based on a ratio of a circumferential direction where defect candidates exist within a predetermined width in a radial direction from a center of the sample.

7. The disk surface inspection method according to claim 6, wherein the defects on the surface of the sample are detected by, regarding the extracted defect candidates, judging connection/continuity of the defect candidates based on position information of the defect candidates on the sample; and extracting the circumferential defect using the judged connection/continuity information of the defect candidates.

8. The disk surface inspection method according to claim 6, wherein regarding defects not judged that the connection/continuity exists in a circumferential shape, it is extracted as a circumferential defect when the ratio in the circumferential direction in which plural defect candidates exist in the range of the predetermined width in the radial direction from the center of the sample is equal to or greater than a previously set ratio.

9. The disk surface inspection method according to claim 6, wherein the defects on the surface of the sample are detected by:

calculating feature amounts of defect candidates other than that extracted as a circumferential defect, from the extracted defect candidates; and classifying the defect candidates as a linear defect, a surface defect, and a plurality of types including foreign material, based on the calculated feature amounts of the defect candidates.

10. The disk surface inspection method according to claim 6, wherein the processed plurality of types of defects including the circumferential defect on the sample are displayed on a map, on the display screen.

* * * * *